(12) United States Patent
Long et al.

(10) Patent No.: US 11,830,604 B2
(45) Date of Patent: Nov. 28, 2023

(54) SYSTEMS AND METHODS FOR PLANNING MEDICAL PROCEDURES

(71) Applicant: Boston Scientific Scimed, Inc., Maple Grove, MN (US)

(72) Inventors: Jerry T. Long, Jamaica Plain, MA (US); Timothy P. Harrah, Cambridge, MA (US); Brandon W. Craft, Edgewater, MD (US); Elizabeth A. Stokley, Baltimore, MD (US); Sebastian Koerner, Berlin (DE); Erik Sperry, Newburyport, MA (US); Chad Schneider, Owings Mills, MD (US); Mark Hera, Holden, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

(21) Appl. No.: 17/653,768

(22) Filed: Mar. 7, 2022

(65) Prior Publication Data
US 2022/0189610 A1 Jun. 16, 2022

Related U.S. Application Data

(63) Continuation of application No. 15/399,590, filed on Jan. 5, 2017, now Pat. No. 11,302,435.
(Continued)

(51) Int. Cl.
*G16H 30/20* (2018.01)
*A61B 34/00* (2016.01)
(Continued)

(52) U.S. Cl.
CPC .............. *G16H 30/20* (2018.01); *A61B 34/10* (2016.02); *A61B 34/25* (2016.02); *G16H 20/40* (2018.01);
(Continued)

(58) Field of Classification Search
CPC ............... A61B 34/10; A61B 10/25; A61B 2034/101–258; G16H 50/70; G06T 7/0012–194; G06T 7/50–77
See application file for complete search history.

(56) References Cited

U.S. PATENT DOCUMENTS 6,939,138 B2 9/2005 Chosack et al.
8,548,778 B1 10/2013 Hart et al.
(Continued)

FOREIGN PATENT DOCUMENTS

CN 100493471 C 6/2009
EP 1684233 A1 7/2006
(Continued)

OTHER PUBLICATIONS

Thiruchelvam et al., Planning percutaneous nephrolithotomy using multidetector computed tomography urography, multiplanar reconstruction and three-dimensional reformatting, Jan. 2005, BJU International 95, 1280-1284 (Year: 2005).*
(Continued)

*Primary Examiner* — Karen A Hranek
(74) *Attorney, Agent, or Firm* — Bookoff McAndrews, PLLC

(57) ABSTRACT

Computer systems and computer-implemented analysis methods may be used for assistance in planning and/or performing a medical procedure, such as percutaneous nephrolithotomy or percutaneous nephrolithotripsy. The method may include receiving one or more radiographic images of an anatomical structure of a patient, generating a display of the radiographic image(s), generating at least one request for user input to identify features of the anatomical structure, receiving user input identifying the features of the anatomical structure, identifying at least one access plan based on the received user input, and generating a display of the identified access plan(s) associated with the radiographic
(Continued)

image(s). The method may include generating a patient template that indicates an insertion site according to the identified access plan(s).

19 Claims, 7 Drawing Sheets

Related U.S. Application Data

(60) Provisional application No. 62/275,466, filed on Jan. 6, 2016.

(51) Int. Cl.
    *A61B 34/10*     (2016.01)
    *G16H 50/50*     (2018.01)
    *G16H 30/40*     (2018.01)
    *G16H 20/40*     (2018.01)
    *G16H 40/60*     (2018.01)
    *G16H 50/70*     (2018.01)
    *A61B 90/00*     (2016.01)
    *A61B 46/00*     (2016.01)
    *A61B 18/00*     (2006.01)
    *A61B 90/11*     (2016.01)

(52) U.S. Cl.
CPC ............ *G16H 30/40* (2018.01); *G16H 40/60* (2018.01); *G16H 50/50* (2018.01); *G16H 50/70* (2018.01); *A61B 46/00* (2016.02); *A61B 90/11* (2016.02); *A61B 2018/00511* (2013.01); *A61B 2034/105* (2016.02); *A61B 2034/107* (2016.02); *A61B 2090/0807* (2016.02); *A61B 2090/3762* (2016.02); *A61B 2090/3764* (2016.02); *A61B 2090/3937* (2016.02)

(56) References Cited

U.S. PATENT DOCUMENTS

| | | | |
|---|---|---|---|
| 2003/0051362 A1 | 3/2003 | Buckman et al. | |
| 2006/0182328 A1* | 8/2006 | Guendel | A61B 6/032 382/132 |
| 2007/0049861 A1 | 3/2007 | Gundel | |
| 2008/0123922 A1 | 5/2008 | Gielen et al. | |
| 2008/0194945 A1 | 8/2008 | Kukuk et al. | |
| 2009/0222059 A1 | 9/2009 | Hillis et al. | |
| 2009/0259230 A1 | 10/2009 | Khadem et al. | |
| 2009/0274271 A1 | 11/2009 | Pfister et al. | |
| 2010/0191071 A1* | 7/2010 | Anderson | G16H 50/50 703/11 |
| 2010/0295848 A1* | 11/2010 | Grewer | G06T 7/11 382/128 |
| 2012/0120091 A1* | 5/2012 | Koudijs | A61B 34/10 345/589 |
| 2013/0172906 A1 | 7/2013 | Olson et al. | |
| 2013/0218003 A1 | 8/2013 | Rothgang et al. | |
| 2013/0316318 A1* | 11/2013 | Frank | A61B 34/25 434/262 |
| 2014/0039658 A1 | 2/2014 | Bangera et al. | |
| 2014/0270441 A1* | 9/2014 | Baker | A61B 34/10 382/131 |
| 2014/0316259 A1 | 10/2014 | Velusamy et al. | |
| 2015/0100066 A1 | 4/2015 | Kostrzewski et al. | |
| 2015/0100578 A1* | 4/2015 | Rosen | G06Q 10/1093 707/737 |
| 2015/0320509 A1 | 11/2015 | Wei et al. | |
| 2016/0008074 A1 | 1/2016 | Glossop | |
| 2016/0070436 A1 | 3/2016 | Thomas et al. | |
| 2016/0155232 A1* | 6/2016 | Sela | G16H 20/40 382/103 |
| 2016/0166329 A1* | 6/2016 | Langan | A61B 6/4014 600/424 |
| 2016/0374760 A1 | 12/2016 | Liang et al. | |
| 2017/0000567 A1* | 1/2017 | Kim | A61B 10/0233 382/103 |

FOREIGN PATENT DOCUMENTS

| | | |
|---|---|---|
| WO | 2013130529 A1 | 9/2013 |
| WO | 2014032171 A1 | 3/2014 |

OTHER PUBLICATIONS

Dillenseger, J-L et al, "A Visual Computer Tool for Percutaneous Nephrolithotomy Preoperative Planning," 25th Annual International Conference of the IEEE EMBS, Sep. 17-21, 2003.
International Search Report and Written Opinion issued in International App. No. PCT/US2017/012381, dated Mar. 24, 2017 (19 pages).
Kambadakone et al., New and Evolving Concepts in the Imaging and Management of Urolithiasis: Urologists' Perspective, 2010, RadioGraphics, 30: 603-623 (Year: 2010).
Ko et al., "Percutaneous Nephrolithotomy Made Easier: A Practical Guide, Tips and Tricks," BJU Int'l., vol. 101, pp. 535-539 (2007).
Miller et al., "Techniquies for Fluoroscopic Percutaneous Renal Access," J. Urology, vol. 178, pp. 15-23 (2007).
Muller et al., "Mobile Augmented Reality for Computer-Assisted Percutaneous Nephrolithotomy," Int. J. CARS, DOI 10.1007/s11548-013-0828-4 (2013).
Ordon et al., CUA Guideline: Managementof ureteral calculi, Dec. 14, 2015, Can Ural Assoc J, vol. 9, Issues 11-12, E837-51 (Year: 2015).
Rassweiler et al., "iPad-Assisted Percutaneous Access to the Kidney Using Marker-Based Navigation: Initial Clinical Experience," Eur. Urology, vol. 61, pp. 628-631 (2012).
Seitel et al., "Computer-assisted trajectory planning for the percutaneous needle insertions," Medical Physics vol. 38, No. 6, dated Jun. 1, 2011.
Sharma et al., "Determining Site of Skin Puncture for Percutaneous Renal Access Using Fluoroscopy-Guided Triangulation Technique," J. Endourology, vol. 23, pp. 193-195 (2009).
Steinberg et al., "Fluoroscopy-Guided Percutaneous Renal Access," J. Endourology, vol. 23, pp. 1627-1631 (2009).
Thiago et al., "Computer Aided Surgery for Percutaneous Nephrolithotomy: Clinical Requirement Analysis and System Design," 32nd Annual International Conference of the IEEE EMBS, Aug. 31-Sep. 4, 2010.
Li et al., Construction of a three-dimensional model of renal stones: comprehensive planning for percutaneous nephrolithotomy and assistance in surgery, Dec. 8, 2021, World Journal of Urology, 31:1587-1592 (Year: 2012).

* cited by examiner

SYSTEMS AND METHODS FOR PLANNING MEDICAL PROCEDURES

CROSS-REFERENCE TO RELATED APPLICATIONS

This patent application is a continuation of and claims the benefit of priority to U.S. Nonprovisional patent application Ser. No. 15/399,590, filed on Jan. 5, 2017, which claims the benefit of priority to U.S. Provisional Application No. 62/275,466, filed on Jan. 6, 2016, which are incorporated by reference herein in their entireties.

TECHNICAL FIELD

Various aspects of the present disclosure relate generally to systems and methods useful in planning and/or performing medical procedures.

BACKGROUND

Substantial progress has been made towards increasing the effectiveness of medical treatment while reducing trauma and risks to the patient. Many procedures that once required open surgery now may be done with less invasive techniques that limit the size of incision, thus providing for less recovery time and risks of infection for the patient. Certain procedures requiring biopsy, electro-stimulation, tissue ablation, or removal of native or foreign bodies may be performed through minimally-invasive surgery.

In the field of urology, for example, renal calculi or kidney stones can accumulate in the urinary tract and become lodged in the kidney. Kidney stones are deposits of materials from the urine, typically minerals and acid salts. While smaller stones may pass from the body naturally, larger stones can require surgical intervention for removal. While open surgery was once the standard treatment for the removal of stones, other less invasive techniques, such as ureteroscopy and percutaneous nephrolithotomy/nephrolithotripsy (PCNL), have emerged as safer, effective alternatives. Yet, procedures such as PCNL still carry risks.

Minimally-invasive procedures like PCNL offer benefits in patient recovery, but afford the physician only a limited view of the treatment site. As a result, it may be difficult to gain sufficient access to a targeted site without causing collateral injury to the patient. Without sufficient knowledge of the patient's anatomy, a physician may need several attempts to properly position and orient the instruments to remove the stone. If the stone is larger or more difficult to grasp than expected for the first route of access, a secondary route of access may be necessary. Repeated attempts at access increase the risk of collateral injury to blood vessels, surrounding tissue, and neighboring organs, and can increase the likelihood of hemorrhage, infection, and fluid leakage/sepsis.

Medical personnel who do not routinely perform PCNL procedures may be especially anxious at the possibility of injury due to improper triangulation to the stone. While patient images like computer tomography (CT) scans may be available for reference beforehand, they often are obtained weeks or months before the PCNL procedure. The stone may have grown in size and/or changed position during the interim, thus adding further uncertainty to successfully removing the stone with minimal harm to the patient.

SUMMARY

The present disclosure includes a method for determining a patient-specific surgical access plan for a medical procedure using at least one computer system, the method comprising receiving over an electronic network, at the at least one computer system, one or more radiographic images of an anatomical structure of a patient; generating a display of the one or more radiographic images; generating at least one request for user input to identify features of the anatomical structure in the one or more radiographic images; receiving a first user input identifying the features of the anatomical structure; identifying, by the at least one computer system, at least one access plan for performing the medical procedure based on the received user input; and generating a display of the identified at least one access plan associated with the one or more radiographic images. In some examples, the medical procedure may be percutaneous nephrolithotomy or percutaneous nephrolithotripsy, and the anatomical structure may be a kidney.

According to some aspects, the one or more radiographic images may include images obtained by computer tomography. The display may include, for example, a three-dimensional representation of the anatomical structure, which may be reconstructed from computer tomography and/or other imaging methods. The radiographic image(s) need not be obtained by computer tomography, or may include additional images obtained by imaging techniques other than computer tomography.

The method may further comprise one or more additional steps. For example, the method may further comprise modifying the one or more radiographic images based on the first user input. Modifying the one or more radiographic images may include, for example, comparing the one or more radiographic images to reference patient data for the medical procedure. Additionally or alternatively, the method may comprise manually and/or automatically identifying one or more features of the anatomical structure in the one or more radiographic images before generating the at least one request for user input.

In some examples, generating the at least one request for user input includes asking a user to identify and/or confirm a location of a kidney stone in the one or more radiographic images. Further, for example, the method may include calculating, by the at least one computer system, at least one characteristic of the kidney stone based on the radiographic image(s). According to some aspects, the characteristic(s) may be chosen from stone burden, stone density, skin to kidney capsule distance, skin to kidney stone distance, or a combination thereof. Other characteristics of the kidney stone may be calculated, identified, or otherwise determined. Identifying the at least one access plan may include calculating a needle trajectory based on the calculated at least one characteristics of the kidney stone.

According to some aspects, the method may comprise generating a patient template that indicates one or more sites (e.g., insertion site(s) for inserting a needle) according to the identified access plan(s). The access plan(s) may include a location and a depth for inserting a needle at the insertion site, e.g., such that the access plan(s) identify a suitable position for the needle to access the patient's anatomy for performing the medical procedure. Generating the patient template may include, for example, printing one or more markings identifying the insertion site to a sheet or other material suitable for transfer to a patient prior to the medical procedure. For example, generating the patient template may include printing at least a first marking identifying the insertion site according to the access plan and a second marking providing a reference relative to one or more anatomical features of the patient. Additionally or alternatively, the at least one access plan may include information on a trajectory of the needle for insertion at the insertion site.

According to some aspects of the present disclosure, the method may comprise performing the medical procedure by inserting a needle at an insertion site according to the at least one access plan. The insertion site may be identified by a light source, e.g., a laser light source or other light source of an imaging device, which may be directed towards the skin of the patient. The light source may be in communication with the electronic network.

BRIEF DESCRIPTION OF THE FIGURES

The accompanying drawings, which are incorporated in and constitute a part of this specification, illustrate various exemplary embodiments and together with the description, serve to explain the principles of the disclosed embodiments.

DETAILED DESCRIPTION

Embodiments of the present disclosure include systems and methods to facilitate, and improve the efficacy and safety of minimally-invasive surgeries. For example, aspects of the present disclosure may provide a user (e.g., a physician, medical technician, or other medical service provider) with the ability to manipulate patient-specific data to analyze and/or simulate different aspects of a medical procedure. In some embodiments, for example, the present disclosure may be used in planning and/or performing a PCNL procedure.

Figure 1:
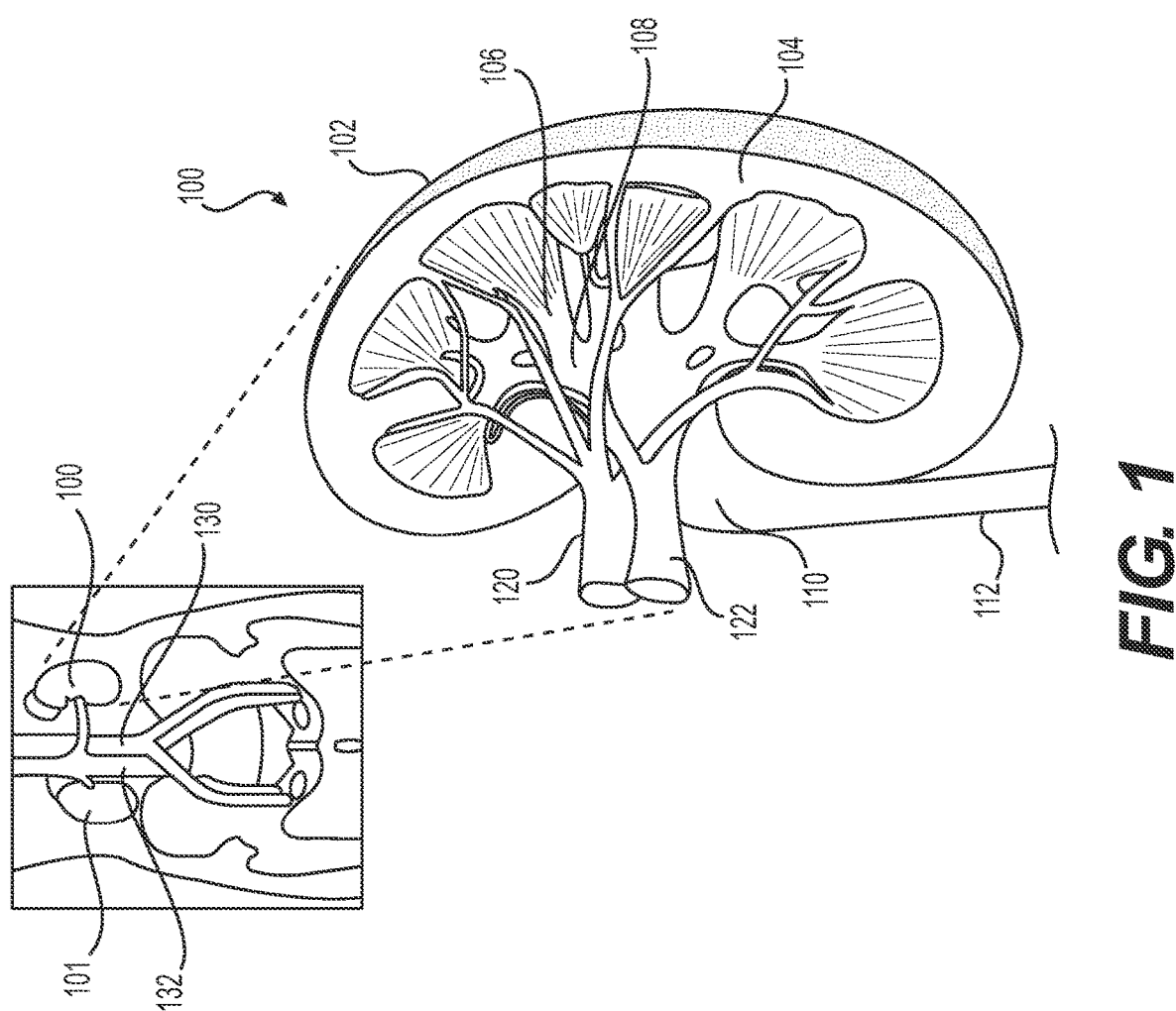
FIG. 1 illustrates anatomical features of a kidney.

PCNL is a minimally-invasive procedure for removing stones from the kidney, and is generally used when other techniques such as ureteroscopy or extracorporeal shock wave lithotripsy are not suitable. For example, PCNL may be appropriate for larger-sized stones (e.g., stones larger than about 2 cm in diameter) or stones that are disposed near the pelvis. FIG. 1 illustrates the location and structure of a kidney 100. The left and right kidneys 100, 101 are located toward the rear of the abdominal cavity, and connected to the circulatory system through the abdominal aorta 130 and the inferior vena cava 132. The renal capsule 102 is tough fibrous tissue that houses the parenchyma 104, the inner tissue of the kidney 100. A series of minor calyces 106 channel urine into major calyces 108, leading into the renal pelvis 110, which becomes the ureter 112. The renal artery 120 and renal vein 122 supply blood to blood vessels disposed throughout the parenchyma tissue 104.

In a typical PCNL procedure, a small incision (~0.5-1.5 cm in diameter) is made in the patient's back through the skin overlying the affected kidney. A small needle is then inserted and advanced into the kidney proximate the stone, and a guide wire is passed through the needle. The needle is then removed with the guide wire remaining in place, and a nephroscope is inserted over the guide wire and positioned proximate the stone as the guide wire is withdrawn. The nephroscope typically includes a light source, an imaging device, and a working channel for suction/irrigation or use of auxiliary instruments to capture and remove the stone. If the stone cannot be removed directly (nephrolithotomy), it may be broken into smaller pieces or fragments (nephrolithotripsy), e.g., via ultrasound, laser, or electrohydraulic techniques, to facilitate removal.

One of the more challenging aspects of PCNL is insertion and proper placement of the needle. Improper positioning could risk puncturing a blood vessel resulting in hemorrhage, cause damage to neighboring organs or tissues, or ultimately place the nephroscope in an incorrect position to access the stone. A detailed understanding of the patient's anatomy and potential access routes may allow the physician to sufficiently prepare for the procedure.

The systems and methods disclosed herein may facilitate collecting, retrieving, analyzing, and/or manipulating patient images and other data to facilitate a PCNL procedure. In some embodiments, the systems and methods disclosed herein may enable a physician to identify, evaluate, and/or simulate different surgical access plans, e.g., pathways or access routes through a patient's anatomy, for retrieving the stone. For example, the physician may execute a computer application via an electronic device to process images and/or retrieve processed images for identifying the presence of a stone and determining the dimensions, density, composition, location, orientation, and/or position of the stone relative to the kidney and surrounding anatomy. Further, in some embodiments, the application may identify and/or simulate one or more access plans associated with the patient images. For example, the application may generate one or more access plans and associate the access plan(s) with the patient images, e.g., by displaying the access route(s) over the patient images. Additionally or alternatively, the application may allow the physician to identify and/or draw one or more access plans on the patient images. The application may be available to the physician in advance of the procedure (e.g., for planning a route of access based on the location/characteristics of a stone), during the procedure (e.g., for comparing to real-time imaging to confirm a pre-determined access route and location/characteristics of the stone), and/or after the procedure (e.g., for further post-operative analysis of the access route taken during the procedure).

Figure 2:
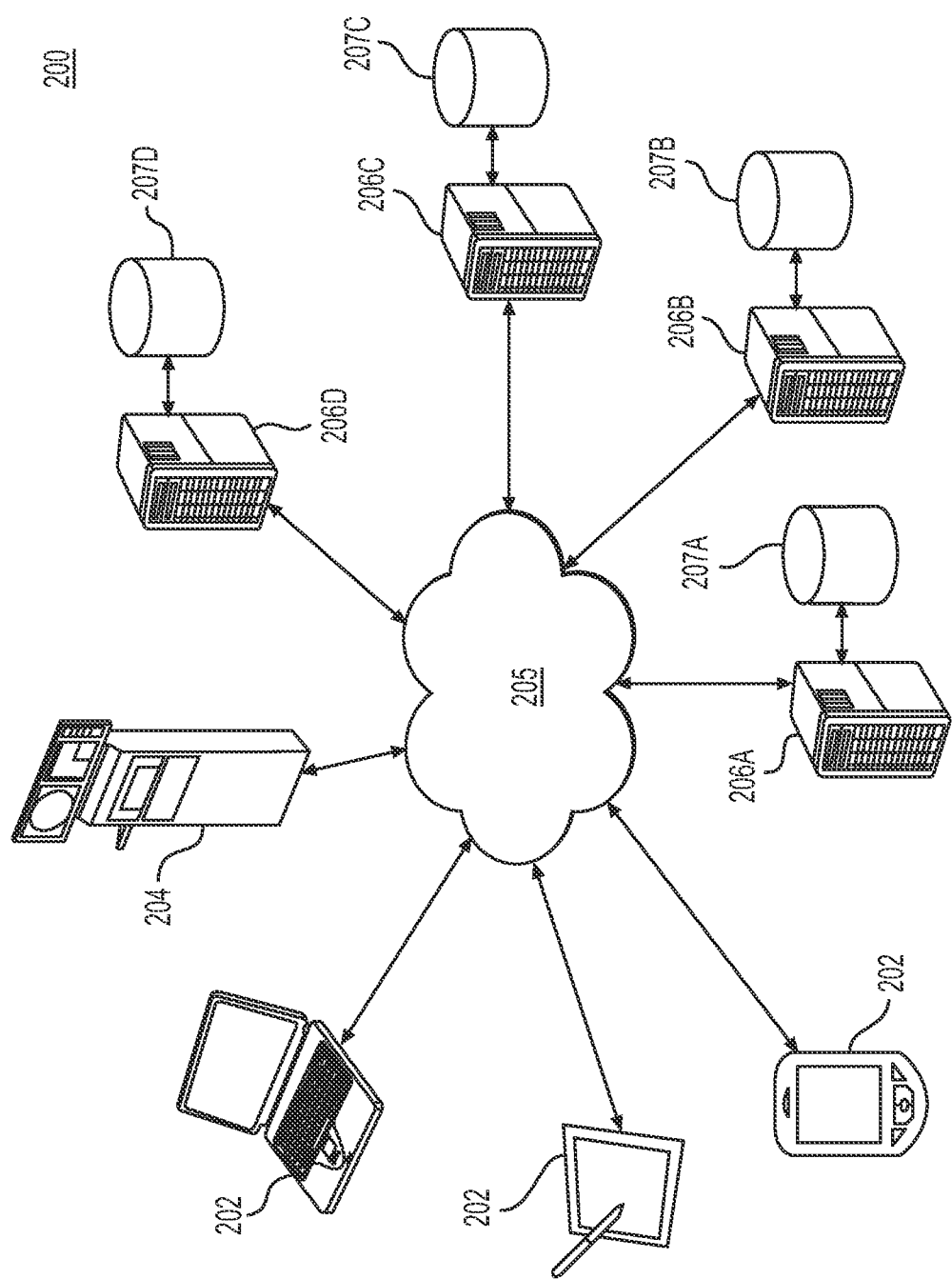
FIG. 2 is a schematic diagram of a system and environment for processing and displaying patient data, in accordance with aspects of the present disclosure.

FIG. 2 shows a schematic diagram of an exemplary computer system and environment for collecting, processing, and displaying patient-specific data according to an exemplary embodiment of the present disclosure. The computer system 200 may include one or more user devices 202 for accessing and/or manipulating data and one or more servers, e.g., servers 206A, 206B, 206C, 206D (each of which may have a corresponding database 207A, 207B, 207C, 207D), in communication with an electronic communication network 205. The network 205 may include the Internet, a virtual private network, or any other combination of wired and/or wireless electronic communication networks. The system 200 also may include one or more imaging devices 204 for obtaining and accessing medical images of a patient.

Each user device 202 may be a stationary or mobile electronic device, including electronic computing devices. Non-limiting examples of such electronic devices include laptop computers, desktop computers, tablet computers (including, e.g., Apple iPad, Samsung Galaxy, Amazon Kindle, and Microsoft Surface devices), smartphones, digital cameras. Non-limiting examples of imaging devices 204 include CT scanners, stationary fluoroscopy machines, mobile C-arm devices, and other angiographic/radiographic devices, as well as cameras, ultrasound (transducer) devices, and magnetic resonance imaging (MRI) machines.

Figure 5:
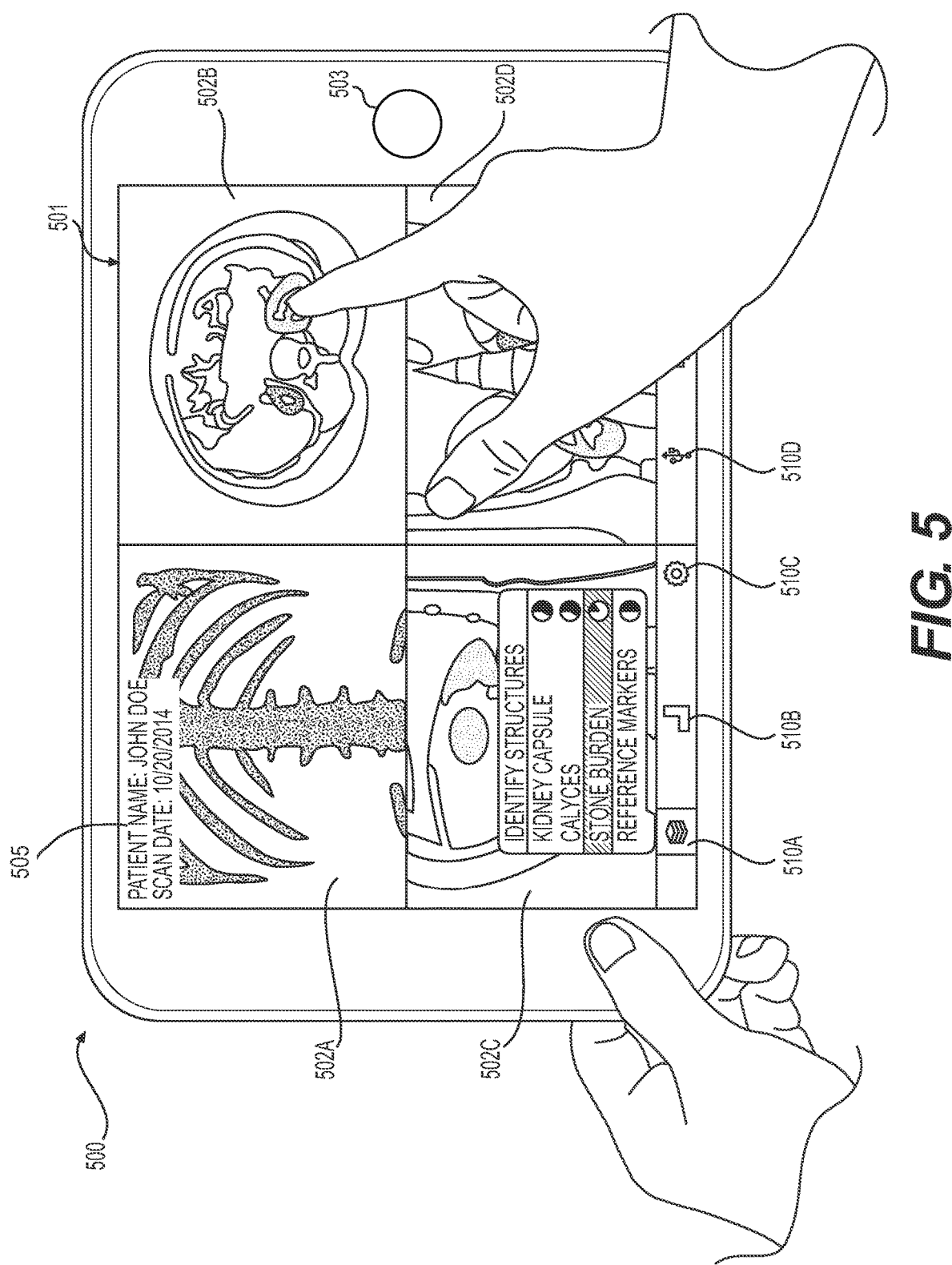
FIGS. 5 and 6 show exemplary screenshots of a graphical user interface, in accordance with aspects of the present disclosure.
Figure 6:
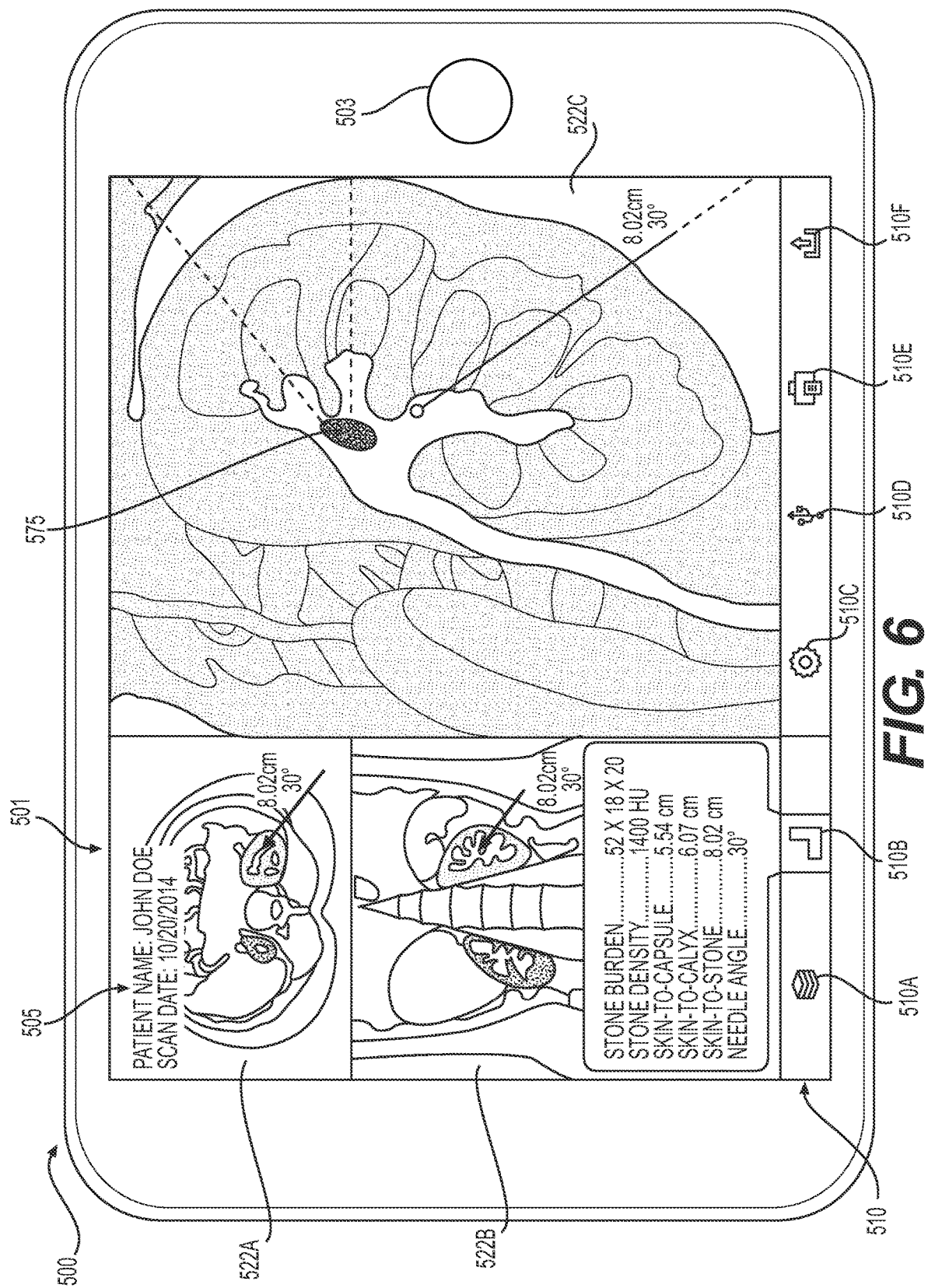

Each user device 202 may include a processor, memory, a display, one or more user input devices, and a network communication interface. The user input device may be, e.g., a display monitor, touchpad, touchscreen, keyboard, or mouse, among other types of devices and device features providing for user input/output capability. The user device(s) 202 may include a display or graphical user interface for receiving user input and displaying data through an application program ("app"). Exemplary screenshots of a user device in the form of a tablet computer 500 are shown in FIGS. 5 and 6, discussed below. The user device(s) 202 may implement appropriate security protocols, such as requiring the user to enter logon credentials to limit access to patient data and comply with applicable health regulations, such as the Health Insurance Portability and Accountability Act (HIPAA).

Each user device 202 and imaging device 204 may be configured to send and/or receive data, including patient data, over the network 205. The patient data obtained and/or accessed over the network 205 may include, but is not limited to, any imaged, detected, measured, processed, and/or calculated physiological data including, e.g., data for various features of the urinary, musculoskeletal, gastrointestinal, dermatological, respiratory, or vascular systems. For example, the patient data may include one or more images of the left and/or right kidneys and surrounding anatomy, such as the left and/or right ureters, renal arteries, renal veins, pelvis, spine, adrenal glands, bladder, and/or urethra. Each image may be associated with the time, date, location, and/or instrument with which the image was taken. In some embodiments, the patient data may include biographical information (e.g., patient name, age, gender, etc.) and/or other physiological health parameters (e.g., average heart rate, body temperature, etc.).

Various medical imaging techniques may be used to collect patient data. For example, images may be generated by a CT scanner and/or by rotational angiography. CT scans generally provide a series of cross-sectional images or "slices" taken at different angles while the patient is immobile, wherein the slices may be assembled into a three-dimensional (3D) image. Rotational angiography may be performed during surgery, e.g., by a mobile C-arm, or while a patient is immobile, but are generally of lower quality than CT scans. For some imaging procedures, a contrast agent may be used to assist in identifying anatomical features in the images. For example, a contrast agent may be introduced into the patient (e.g., via the patient's urinary tract via the ureter) prior to imaging to assist in visualization of the kidneys and urinary system.

Figure 3:
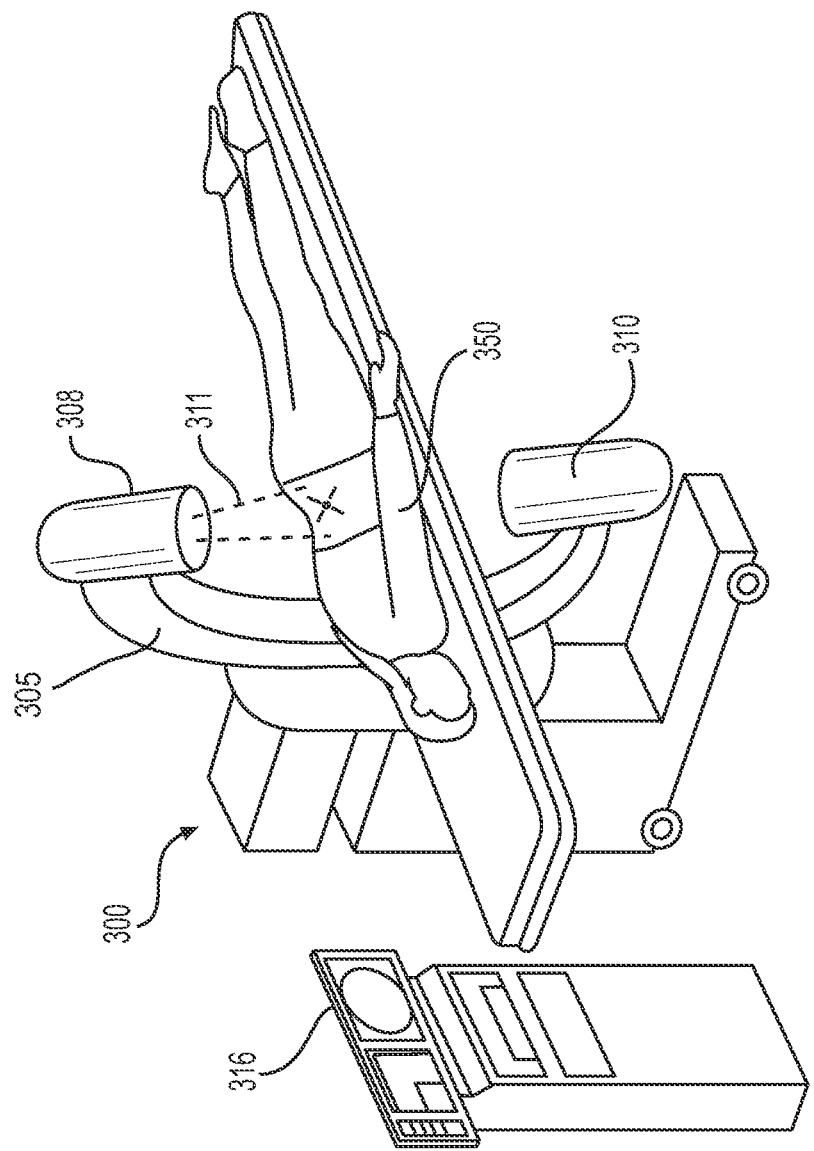
FIG. 3 shows an exemplary imaging device, in accordance with aspects of the present disclosure.

FIG. 3 illustrates an exemplary mobile C-arm device 300 useful for collecting X-ray images of a patient 350 in preparation for and/or during a PCNL procedure, according to some aspects of the present disclosure. As shown, the "C-arm" 305 of the imaging device 300 includes an X-ray tube 308 aligned with a detector 310 positioned on the opposite side of the patient 350. The C-arm 305 may be rotatable relative to the patient in one or more planes (e.g., about an axis parallel and/or an axis perpendicular to the patient 350) to allow for the collection of images in different orientations, without moving the patient 350. The images may be displayed and analyzed in real time on a monitor or display 316 of the imaging device 300 and/or may be stored locally or remotely for later viewing and analysis. For example, the C-arm device 300 may be used to collect patient images during a PCNL procedure, e.g., wherein the physician may consult the images for guidance on proper positioning of the insertion needle, nephroscope, and other instruments during the procedure.

The mobile C-arm device 300 may include a light source to identify a specific target or region of a patient, such as an intended incision or insertion site. For example, the C-arm 305 may include a light source coupled to or incorporated into the X-ray tube 308, wherein the light source may be used to direct light on a pre-determined insertion site for a PCNL procedure. FIG. 3 illustrates light 311 focused on the back of the patient 350 in the form of an "X" or crosshairs to indicate the intended site of insertion. The direction, orientation, intensity, and/or shape of the light generated by the light source may be controlled via user input at the display 316 and/or by instructions received over the network 205, as discussed further below.

Returning to FIG. 2, the servers 206A-206D may be configured to receive patient data over the network 205, e.g., from user devices 202, imaging devices 204, other servers, and/or a shared cloud network. Each server 206A-206D may perform different functions, or certain functions may be shared by two or more servers 206A-206D. Each server 206A-206D may include a processor and memory for executing and storing processor-readable instructions. One or more of the servers 206A-206D may be communicatively coupled to a corresponding database 207A-207D configured to store data (e.g., patient data) accessible to the server 206A-206D. At least one server 206A-206D may include a data analyzer configured to perform analysis of received data and/or an application program that allows a physician to control analysis parameters, such as threshold values used by the data analyzer in performing the analyses.

In some embodiments, the system 200 may include an imaging server 206A, a patient records server 206B, a reference data server 206C, and an application server 206D. As mentioned above, more or fewer servers may be used. For example, in some embodiments, the functions performed by imaging server 206A, patient records server 206B, reference data server 206C, and application server 206D (or any combination thereof) may be implemented by a single server.

The imaging server 206A may receive, process, and/or transmit patient images for viewing and analysis according to the methods herein. For example, the imaging server 206A may receive images generated by the imaging device(s) 204, perform one or more processing steps, and transmit the processed images for viewing on the user device(s) 202. Additionally or alternatively, the imaging server 206A may retrieve images saved to the database 207A, which may correspond to prior images obtained for the patient. Image processing steps may include, but are not limited to, assembling multiple images into a 3D representation or model, associating images with patient information, grouping together images of similar type and/or date, reducing noise, and/or recognizing/labeling particular anatomical features. Image processing may be performed by appropriate algorithms known generally in the art. In some embodiments, multiple images generated by the same or different devices may be layered (e.g., one image overlaying another) and/or combined into a single two- or three-dimensional image.

The patient records server 206B may be used to retrieve patent-specific information for associating with the images and/or viewing on the user device(s) 202. For example, the patient records server 206B may correspond to a server of the hospital or medical office where the patient has previously received or routinely receives medical treatment. Information received and/or transmitted by the patient records server 206B may include, but is not limited to, the patient's name, date of birth, age, contact information, general medical condition, prior surgeries and other medical events (including prior kidney stone incidence), physiological information (e.g., average blood pressure, average heart rate, etc.), and other patient-specific information that may be helpful to a physician in planning a PCNL procedure or other medical procedure. In some embodiments, the patient records server 206B may retrieve patient information from records stored in database 207B.

The reference data server 206C may be used to access relevant data from medical case studies for reference and/or comparison to the patient data. For example, aggregated data from medical case studies may be used to automatically identify different features in the patient images (e.g., the renal capsule, the major/minor calyces, and renal pelvis of the kidney, and/or possible location of a kidney stone). In some embodiments, the reference data server 206C may compare the patient data to various case study data (e.g., the case study records optionally saved in database 207C) to attempt to locate one or more reference patient profiles. For example, the reference patient profile(s) may include information on the removal of kidney stones of similar size and/or location as that of the patient.

The application server 206D may communicate with the user device(s) 202 to transmit and/or receive instructions for generating and displaying patient data tailored to the user's preferences and needs. The application server 206D may assemble the patient data, e.g., from other servers 206A-206C, imaging device(s) 204, and perform analyses, calculations, and/or generate simulations as needed. For example the application server 206D may send instructions to the user device(s) 202 to prompt the user for input, and may process data received from one or more other servers 206A-206C (or information saved in database 206D) based on the user input to modify the information displayed on the user device(s) 202 accordingly.

Figure 4:
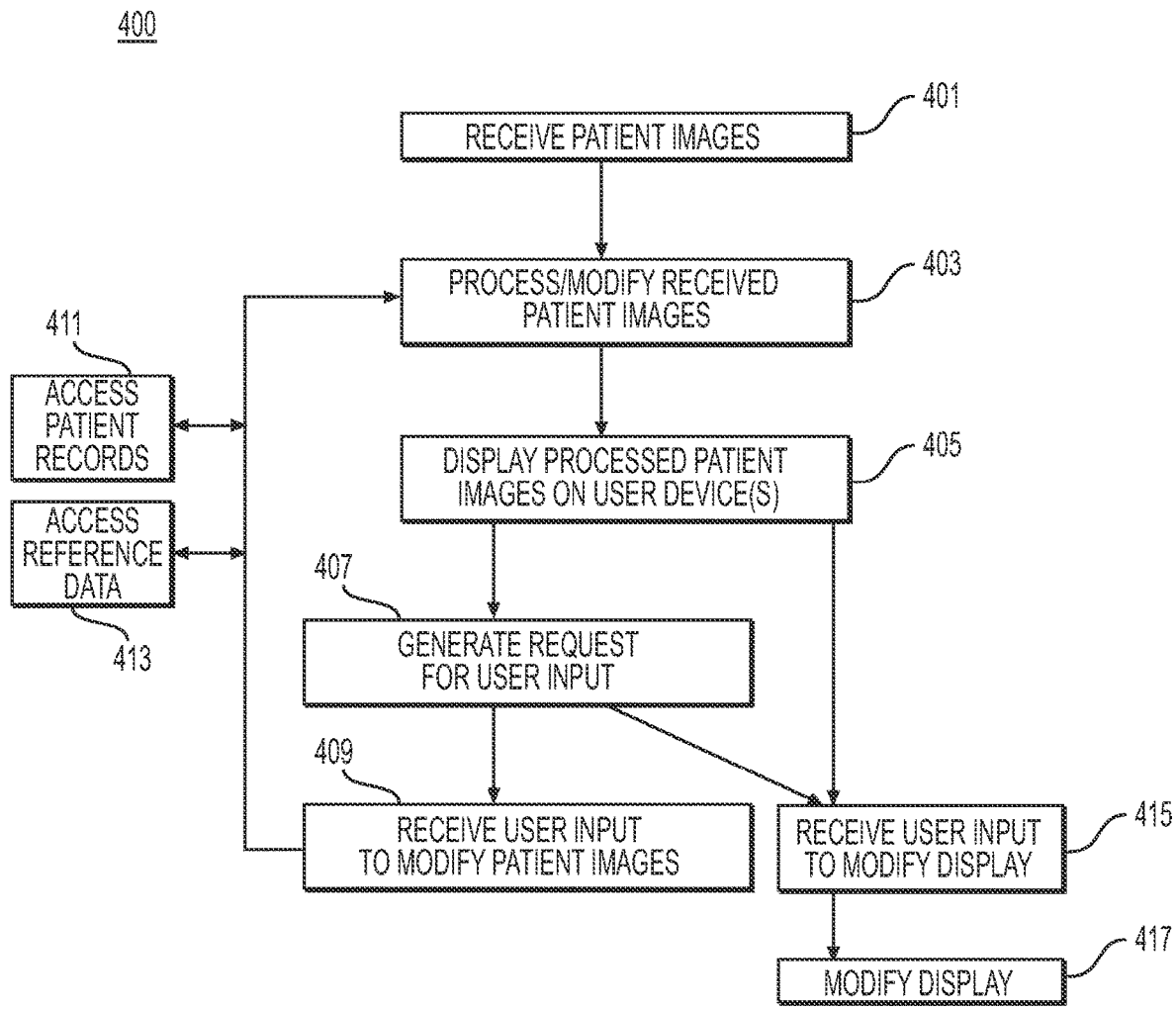
FIG. 4 is a flow diagram of an exemplary method for processing and displaying patient data, in accordance with aspects of the present disclosure.

FIG. 4 shows a flow diagram of an exemplary method 400 for collecting, processing, and displaying patient data, using the system of FIG. 2. Method 400 may include receiving patient images (step 401), such as from an imaging device 204 and/or the imaging server 206A discussed above. The received patient images then may be processed (step 403), e.g., via the imaging server 206A and/or application server 206D. Step 403 may include any of the processing/modification techniques discussed above. In some embodiments, for example, step 403 may include generating a 3D representation of the kidney and surrounding anatomy from received CT scans, automatically identifying different features of the kidney and/or surrounding tissues, and/or automatically identifying one or more access plans for removing a kidney stone.

The processed/modified images then may be displayed on one or more user devices 202 (step 405), such as a tablet computer. Next, a request for user input may be generated (step 407), e.g., as a prompt on the screen of the tablet computer. For example, the screen may show a text box asking the user to identify and/or confirm specific structures of the kidney and the location of any kidney stones, e.g., by touching the screen. In some embodiments, the user may be prompted to draw an access plan and/or highlight one or more portions of an access plan, e.g., by dragging a digit (finger or thumb), or a stylus across the screen.

In some embodiments, the user input may include a request to further process/modify the patient images (step 409). For example, the user device 202 may receive a user request to calculate the dimensions and/or density of a stone that the user has marked, or to generate a new 3D model of the kidney based on a different selection of images, a different algorithm, or other parameters. Thus, the method may include repeating step 403 one or more times. In some embodiments, processing/modifying the patient images may include accessing patient records (step 411) and/or accessing reference data (step 413), such as case study information as discussed above. The processed images again may be displayed on the user device(s) 202 (step 405).

In some embodiments, the user input may not require further processing of the images. For example, the user may wish to manipulate the images that have already been processed and displayed on the user device(s) 202, e.g., to magnify, miniaturize, and/or rotate an image or portions of an image, to browse through a series of images (e.g., individual slices from a CT scan), and/or to change the layout of multiple images as displayed on the user device(s) 202. Upon receiving user input to modify the display (step 415), the user device 202 may perform the corresponding function to perform the modification (step 417).

Each user device 202 may have an appropriate interface or controls to allow the user to select different options for manipulating patient images. For example, the user may select from menu options via a keyboard or mouse, or via a touchscreen. For user devices 202 with a touchscreen, such as some smartphone and tablet computers, the user device 202 may be configured to associate the type of user input with a particular function. For example, the user device 202 may be configured to determine when the user's fingers pinch the surface of the touchscreen. If the user's fingers move closer together, the user device 202 may zoom out from the displayed images, whereas if the user's fingers move away from each other, the user device 202 may zoom in on the images being displayed. The amount of the zoom may depend on the distance that the finger(s) travel in the pinch along the surface of the touchscreen.

The user device(s) 202 may communicate with one or more of the servers 206A-206D over the network 205 as discussed above to transmit data such as user instructions and/or receive data such as patient images (including any processed images) and other patient data, reference data, or instructions to generate a prompt requesting user input. In some embodiments, the user device(s) 202 may be configured to perform some or all image processing or other data processing functions.

FIGS. 5 and 6 illustrate exemplary user interfaces of a tablet computer 500 as an exemplary user device 202 according to some embodiments of the present disclosure. The tablet computer 500 may have a touchscreen configured to receive input from the user based on contact by at least one of the user's digits (e.g., one or more fingers or thumbs) on a surface of the touchscreen. It is understood that the touchscreen may be configured to receive input from the user based on contact or sensed proximity to the touchscreen by the user's finger(s), the user's thumb(s), a stylus, another pointing object or instrument, or a combination thereof. Further, it is understood that user devices 202 according to the present disclosure need not have a touchscreen, but may receive user input through other input devices known in the art, including the user input devices mentioned above.

The tablet computer 500 may include a display 501 for displaying information and a user element 503, which may allow the user to exit the application and/or power on/off the tablet computer 500. The display 501 may show one image or multiple images, e.g., separated into different panels. For example, FIG. 5 shows the display 501 divided into four panels 502A, 502B, 502C, and 502D, and FIG. 6 shows the display 501 divided into three panels 522A, 522B, and 522C. The panels may have the same or substantially the same size and shape, as in FIG. 5, or may have different shapes and/or different dimensions relative to the other panels, as shown in FIG. 6. Different types of images may be shown in the various panels, e.g., to highlight various anatomical structures and features. The panels may show raw data (e.g., raw images collected via CT scan, X-ray, fluoroscopy, or rotational angiography), manipulated/processed data (including, but not limited to, simplified images or access plans/representations, annotated images, layered image data), simulated data (including, but not limited to, 3D simulations, access plans/representations with simulated access routes, and raw or processed images with simulated features). The panels may include annotations generated by the system or provided by user input to identify features and/or provide information or various metrics for reference. For example, the panels may show density information, stone burden, and/or skin-to-stone distance, among other metrics.

For example, the different panels may show one or more X-ray images, one or more CT images, which may be collected at different angles providing for planar views in various x, y, z coordinates (e.g., coronal, sagittal, and transverse views), and/or one or more fluoroscopic images. These different views may assist a user in determining the position and/or size of kidney stones. For example, the user may use the different views to mark various features of the kidney, so that multiple CT image views may be combined to visualize the structure of the kidney in three dimensions. FIG. 5 shows a transverse CT image in panel 502B, a sagittal CT image in panel 502C, a coronal CT image in panel 502D, and a kidney-ureter-bladder X-ray in panel 502A. FIG. 6 shows a transverse CT image in panel 522A (which may be the same image shown in panel 502B of FIG. 5), a coronal CT image in panel 522B (which may be the same image shown in panel 502D of FIG. 5), and a 3D image in panel 522C reconstructed from CT data, showing a kidney, its calyces, and a kidney stone. The user may be able to manipulate the 3D image, such as by rotating the image and/or zooming in or out on particular features or regions of interest. For example, the user may manipulate the 3D image to view different angles of needle insertion by rotating the image and/or zooming in or out on particular features.

The display 501 may include a menu 510 with one or more menu options (icons 510A-510F, as shown) to allow the user to select among different options for displaying and/or processing the images. For example, a first menu option 510A may be selected to identify and/or characterize different anatomical structures or features shown. An exemplary list of items is shown in FIG. 5, including the kidney capsule, calyces of the kidney, the kidney stone burden (the size of the stone), and/or the location of any reference markers. The list may include a progress indicator for each item showing whether additional user input is desired or required. The user may select identify different features using the touchscreen, wherein the user device 202 and/or other components of the system 200 may use image recognition algorithms to identify/outline the entire structure (e.g., by detecting surrounding areas of the same contrast level).

A second menu option 510B may allow a user to view data corresponding to a particular feature, such as a kidney stone. FIG. 6 shows a list of data corresponding to a kidney stone 575 shown in the image of panel 522C. The data may be calculated by the system 200, or may be already associated with the patient images. As shown, the data may include the stone burden (e.g., the dimensions of the stone, in mm), the stone density (radiodensity calculated by CT scan, according to the Hounsfield scale), the distances from the patient skin surface to kidney capsule, calyx, and stone 575, and the projected angle for inserting the needle during a PCNL procedure to reach the stone.

A third menu option 510C may allow a user to change various settings, such as sensitivity settings, different algorithms to be used, a default of how many image panels to be shown at initiation of the application, etc. A fourth menu option 510D may indicate information about connectivity to the network 205, a fifth menu option 510E may allow a user to print information such as a surgical template as discussed below, and a sixth menu option 510F may allow a user to upload and/or download patient images or other patient data or information over the network 205. Menu options 510A-510F are intended to be exemplary; the menu 510 may include other types of menu options, and fewer or more menu options than shown.

In some embodiments, portions of the display 501 may show text and/or annotation to the images shown. For example, the text may include information about the patient, information about the images shown on the display 501, or comments from a physician or other medical professional, among other types of information. Further, for example, the annotation may identify various anatomical features or reference markers, or may reflect information about an access plan or projected needle trajectory. Each of FIGS. 5 and 6 show a text box 505 overlaying a portion of the display 501 with information about the patient (patient name) and the images shown (the date the images were obtained). FIG. 6 further shows annotation to the images shown in each of panels 522A, 522B, and 522C to indicate a needle insertion depth of 8.02 cm (skin to stone) at an angle of 30 degrees.

As mentioned above, the system 200 may allow a physician or other user to identify and evaluate different access plans. The system 200 may identify one or more access plans automatically (e.g., during the processing of images, step 403 of method 400) and/or may highlight various access plans upon user input. For example, the user may select different images and/or rotate a 3D representation of the kidney to assess different pathways to reach the stone, and may draw or highlight a chosen access plan by dragging a digit (finger or thumb) or stylus across the screen. Upon detecting the dragging motion, the user device 202 and/or other components of the system 200 may use image recognition algorithms to identify/outline the entire pathway, e.g., identifying each access plan in a different color. A user may choose a desired access plan, whereupon the user device 202 and/or other components of the system 200 may generate a "final" access plan including the location, depth, and trajectory angle(s) with respect to the skin surface at which the needle should be inserted to reach the kidney and stone with minimal injury to the patient.

Figure 7B:
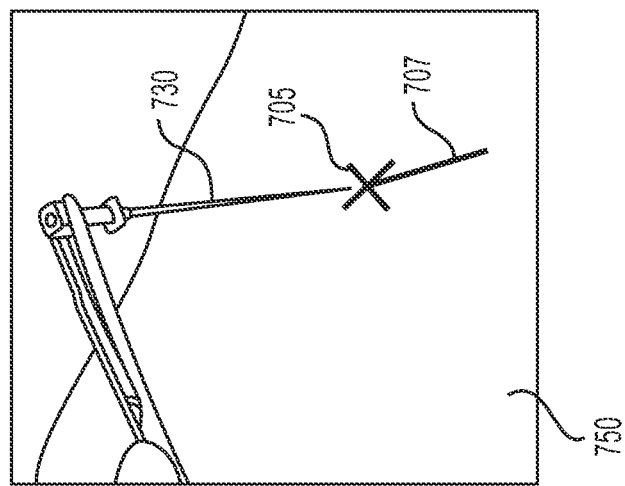
FIGS. 7A and 7B show an exemplary patient template, in accordance with aspects of the present disclosure.
Figure 7A:
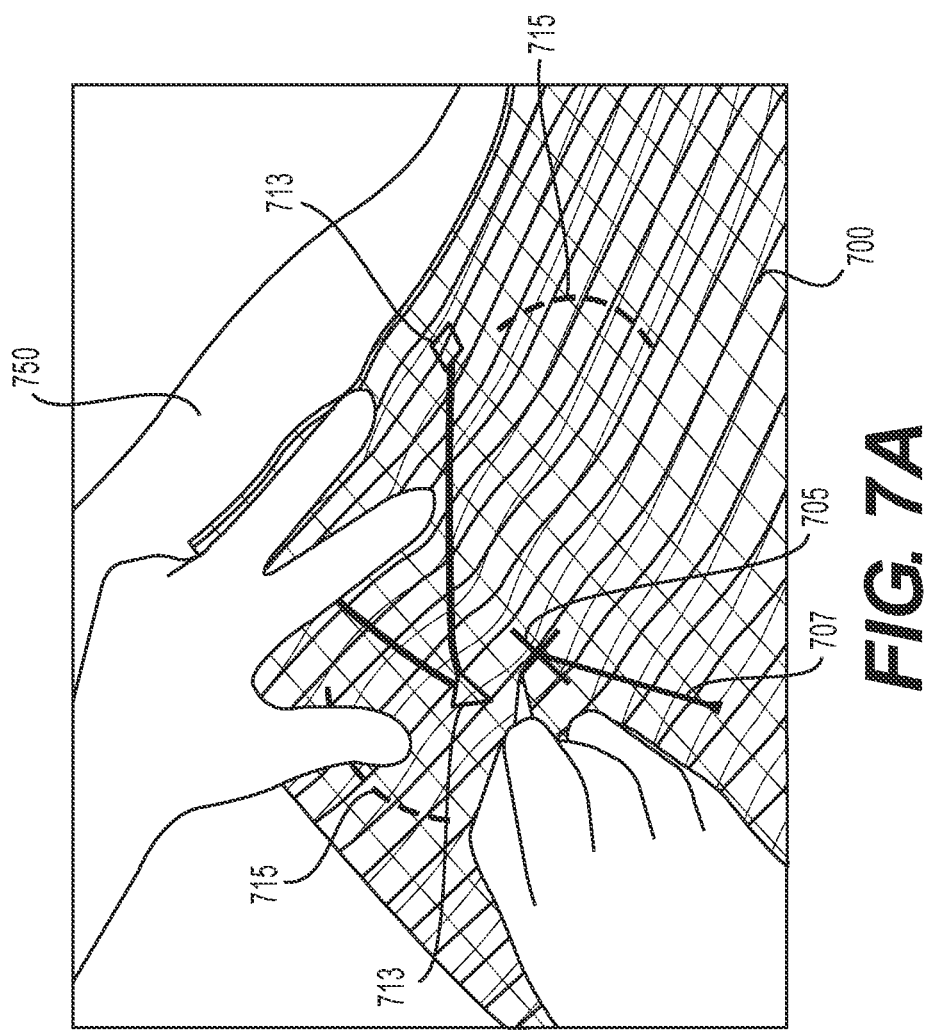

In some embodiments, the user device 202 may allow the user to generate and print a patient template to assist in performing a PCNL procedure. FIGS. 7A and 7B illustrate a patient template 700 according to some aspects of the present disclosure. For example, the patient template 700 may include one or more markings 705 to indicate the location for inserting the needle 730, and one or more markings 707 to indicate the trajectory of the needle 730, according to the access plan generated by the system 200. For example, a first marking 705 (e.g., an X) may identify the location for inserting the needle 730, and a second marking 707 leading away from the first marking 705 (e.g., a line) may identify the trajectory for the needle 730 to follow once inserted. For example, the system 200 may generate an access plan having an angle of 30 degrees (see FIGS. 5 and 6), which may correspond to the angle the needle should make with the patient 750 when aligned with the second marking 707 and inserted at the first marking 705. In some embodiments, the trajectory angle(s) of the needle 730 may be printed on the patient template 700. In some embodiments, the insertion site for the needle 730 also may be indicated by a light source of an imaging device (e.g., a light source coupled to or incorporated into the X-ray tube 308 of a mobile C-arm device 300, as shown in FIG. 3) to be used during the PCNL procedure.

The patient template 700 may include one or more additional markings to provide references for placing the patient template 700 in the correct location on the patient 750. FIG. 7A shows two reference markings 715, represented in this example as curved lines, to assist in placement of the patient template 700 relative to anatomical features, such as the patient's ribs or vertebrae, the location of which may be derived from CT data and palpated pre-operatively. The patient template 700 may be positioned on the patient such that the reference markings 715 match their respective anatomical features to serve as landmarks for correct orientation of the patient template 700.

Additionally or alternatively, the patient template 700 may include reference markings 713 to be aligned with corresponding reference markers (e.g., radiopaque fiducials) placed externally on the patient's skin. For example, one or more reference markers placed at discrete locations on the patient may be visible during imaging, and provide additional triangulation information for proper insertion of the needle 730.

The types and locations of any reference markings 713, 715 of the patient template 700 may be automatically generated by the user device 202 and/or other components of the system 200, or may be added by user input to the user device 202. Further, the patient template 700 may include other information as desired, e.g., to confirm that the patient template 700 is being used with the correct patient 750.

The patient template 700 may be printed on a sheet of porous material, e.g., gauze or polymeric mesh fabric, for transferring the template to the patient 750. The material of the printed patient template 700 may be non-sterile. As shown in FIG. 7B, the various markings 705, 707, 713, 715 then may be traced and transferred to the patient 750. The markings 705, 707, 713, 715 may remain visible after the patient 750 is scrubbed to render the surgical environment sterile for the PCNL procedure.

Other embodiments of the present disclosure will be apparent to those skilled in the art from consideration of the specification and practice of the embodiments disclosed herein. While certain features of the present disclosure are discussed within the context of exemplary systems, devices, and methods, the disclosure is not so limited and includes alternatives and variations of the examples herein according to the general principles disclosed. It is intended that the specification and examples be considered as exemplary only, with a true scope and spirit of the present disclosure being indicated by the following claims.

We claim:

1. A method for determining a patient-specific surgical access plan for a medical procedure, the method comprising:
receiving a plurality of radiographic images of an anatomical structure of a patient;
generating a three-dimensional representation of the anatomical structure based on the plurality of radiographic images;
identifying an object in the three-dimensional representation;
providing, to a user device for display on the user device, the three-dimensional representation with the object visually indicated and a prompt requesting input via the user device to confirm the object and to identify at least a portion of an access plan for performing a medical procedure to remove the object, wherein providing the prompt requesting user input is based on a selection of a menu option via a user interface displaying the three-dimensional representation, and wherein the prompt includes a text box requesting the confirmation of at least the object;
responsive to the prompt, receiving a first user input confirming the object and a second user input identifying the portion of the access plan on the displayed three-dimensional representation;
identifying at least one access plan for performing the medical procedure based on the first user input and the second user input, wherein the at least one access plan includes the portion of the access plan identified by the second user input; and
providing, to the user device for display, an updated three-dimensional representation with the at least one access plan included.

2. The method of claim 1, wherein identifying the object in the three-dimensional representation comprises:
determining one or more characteristics of the object, the one or more characteristics including a dimension of the object, a density of the object, a composition of the object, a location of the object, or an orientation of the object.

3. The method of claim 2, wherein identifying the at least one access plan for performing the medical procedure is further based on the one or more characteristics of the object.

4. The method of claim 1, further comprising:
receiving, from the user device, third user input manipulating the updated three-dimensional representation; and
providing, to the user device for display, a modified version of the updated three-dimensional representation corresponding to the manipulation.

5. The method of claim 1, further comprising:
receiving patient data associated with the patient;
receiving patient data associated with a plurality of other patients;
comparing the patient data associated with the patient to the patient data associated with the plurality of other patients to identify one or more reference patient profiles; and
identifying the at least one access plan for performing the medical procedure further based on the one or more reference patient profiles.

6. The method of claim 1, wherein the at least one access plan includes an insertion site, and the method further comprises:
generating a patient template that indicates the insertion site, wherein the patient template includes a first marking identifying a location for needle insertion and a second marking identifying a needle trajectory following insertion.

7. The method of claim 1, wherein the at least one access plan includes an insertion site, and the method further comprises:
providing a location of the insertion site to an imaging device, the imaging device comprising a light source operable to direct light on the location of the insertion site.

8. The method of claim 1, wherein the anatomical structure includes a kidney and surrounding anatomy, the object includes a kidney stone, and the medical procedure is a percutaneous nephrolithotomy or percutaneous nephrolithotripsy.

9. The method of claim 1, wherein the anatomical structure is a kidney, the object intended to be identified in the three-dimensional representation is a kidney stone, and the text box requests confirmation that the object identified is the kidney stone.

10. A method for determining a patient-specific surgical access plan for a medical procedure, the method comprising:
receiving a plurality of radiographic images of an anatomical structure of a patient;
generating a three-dimensional representation of the anatomical structure based on the plurality of radiographic images;
providing the three-dimensional representation to a user device for display;
one of automatically identifying an object in the three-dimensional representation or receiving additional user input identifying the object in the three-dimensional representation, wherein the object is to be removed as part of the medical procedure;
determining and providing, to the user device for display, one or more characteristics of the object identified within the three-dimensional representation based on a selection of a menu option via a user interface displaying the three-dimensional representation on the user device, wherein the one or more characteristics of the object include a dimension of the object, a density of the object, a composition of the object, or an orientation of the object;
receiving, from the user device, user input including a partial path provided across a portion of the displayed three-dimensional representation, the partial path designating a portion of an access plan for performing a medical procedure;
automatically identifying, using one or more image recognition processes and the partial path, a remaining portion of the access plan for performing the medical procedure, wherein the automatically identifying the remaining portion of the access plan is further based on the one or more characteristics of the object; and
providing an updated three-dimensional representation including an entirety of the access plan to the user device for display, the entirety of the access plan comprising the portion of the access plan designated by the partial path included in the user input and the automatically identified remaining portion.

11. The method of claim 10, wherein the object in the three-dimensional representation is automatically identified, and the method further comprises:
providing, to the user device for display, a prompt requesting input via the user device to confirm the object.

12. The method of claim 10, further comprising:
receiving patient data associated with the patient;
receiving patient data associated with a plurality of other patients; and
comparing the patient data associated with the patient to the patient data associated with the plurality of other patients to identify one or more reference patient profiles,
wherein the automatic identifying of the remaining portion of the access plan is further based on the one or more reference patient profiles.

13. The method of claim 10, further comprising:
receiving, from the user device, additional user input manipulating the updated three-dimensional representation; and
providing, to the user device for display, a modified version of the updated three-dimensional representation corresponding to the manipulation.

14. The method of claim 10, wherein the access plan includes a location for needle insertion, and the method further comprises at least one of:
generating a patient template that indicates at least the location for needle insertion for printing and transfer to the patient prior to the medical procedure; or
providing the location for needle insertion to an imaging device, the imaging device comprising a light source operable to direct light on the location during the medical procedure.

15. The method of claim 10, wherein the partial path provided across the portion of the displayed three-dimensional representation is drawn on a screen of the user device via a contacting of a digit or an implement across a surface of the screen.

16. A method for determining a patient-specific surgical access plan for a medical procedure, the method comprising:
receiving a plurality of radiographic images of an anatomical structure of a patient;
generating a three-dimensional representation of the anatomical structure based on the plurality of radiographic images;
providing the three-dimensional representation to a user device for display on a user interface including a plurality of menu options;
in response to receiving, from the user device, an indication of a selection of a first menu option of the plurality of menu options via the user interface, providing a prompt to the user device for display on the user interface, the prompt requesting confirmation of an object identified in the three-dimensional representation via the user interface;
in response to receiving, from the user device, an indication of a selection of a second menu option of the plurality of menu options via the user interface, determining and providing one or more characteristics of the object to the user device for display on the user interface;
receiving, from the user device, a first user input including a partial outline of a route across a portion of the displayed three-dimensional representation, the partially outlined route designating a portion of an access plan for performing a medical procedure;
automatically identifying, using one or more image recognition processes and the partially outlined route, a plurality of access plans for performing the medical procedure, each of the plurality of access plans including the portion of the access plan designated by the partially outlined route included in the first user input and a different option for a remaining portion of the access plan to complete the outline of the route;

providing a first updated three-dimensional representation including each of the plurality of access plans to the user device for display;
receiving, from the user device, a second user input selecting one of the plurality of access plans displayed in the first updated three-dimensional representation; and
providing a second updated three-dimensional representation including the selected one of the plurality of access plans to the user device for display.

17. The method of claim 16, further comprising:
one of automatically identifying the object in the three-dimensional representation or receiving additional user input identifying the object in the three-dimensional representation, wherein the object is to be removed as part of the medical procedure,
wherein the one or more characteristics of the object includes a dimension of the object, a density of the object, a composition of the object, a location of the object, or an orientation of the object, and
wherein the automatic identifying of the plurality of access plans for performing the medical procedure is further based on the one or more characteristics of the object.

18. The method of claim 16, wherein the selected one of the plurality of access plans includes a location for needle insertion, and the method further comprises at least one of:
generating a patient template that indicates at least the location for needle insertion for printing and transfer to the patient prior to the medical procedure; or
providing the location for needle insertion to an imaging device, the imaging device comprising a light source operable to direct light on the location during the medical procedure.

19. The method of claim 16, wherein the three-dimensional representation is annotated with at least one of the one or more characteristics provided for display.

\* \* \* \* \*